(12) United States Patent
Arduino et al.

(10) Patent No.: US 7,422,844 B2
(45) Date of Patent: Sep. 9, 2008

(54) SOLUTION FOR THE STORAGE AND PERFUSION OF ORGANS AWAITING TRANSPLANTATION

(75) Inventors: Arduini Arduino, Rome (IT); Aureli Tommaso, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 352 days.

(21) Appl. No.: 10/480,824

(22) PCT Filed: Jun. 13, 2002

(86) PCT No.: PCT/IT02/00391

§ 371 (c)(1),
(2), (4) Date: Dec. 15, 2003

(87) PCT Pub. No.: WO02/102149

PCT Pub. Date: Dec. 27, 2002

(65) Prior Publication Data

US 2004/0156990 A1    Aug. 12, 2004

(30) Foreign Application Priority Data

Jun. 14, 2001 (IT) .......................... RM2001A0337

(51) Int. Cl.
*A01N 1/00* (2006.01)
(52) U.S. Cl. ...................................... 435/1.1
(58) Field of Classification Search ........................ None
See application file for complete search history.

(56) References Cited

U.S. PATENT DOCUMENTS 5,834,178 A * 11/1998 Churchill et al. ............. 435/1.2
RE36,331 E * 10/1999 Arduini .................... 514/228.8

FOREIGN PATENT DOCUMENTS

| WO | 96/18293 | A | 6/1996 |
| WO | 96/40167 | A | 12/1996 |
| WO | 00/30637 | * | 6/2000 |
| WO | 00/30637 | A | 6/2000 |

OTHER PUBLICATIONS

Loster et al., "Effects of L-carnitine and its acetyl and propionyl esters on ATP and PCr levels of isolated rat hearts perfused without fatty acids and investigated by means of 31P-NMR spectorscopy", Molecular and Cellular Biochemistry 200 : 93-102 (1999).*

Boehmova et al., "Renal ischemia-reperfusion injury: an inescapable event affecting kidney transplantation outcome", Folia Microbiologica 46 (4) : 267-276 (2001).*

Kasperk et al., "Morphometric study of centrilobular vessels in the rat liver after continuous perfusion with Euro-Collins and University of Wisconsin solution", Research in Experimental Medicine 194 (6) : 383-90 (1994).*

Rossaro et al., "Phosphorus 31-nuclear magnetic resonance spectroscopy of rat liver during simple storage or continuous hyptothermic perfusion", Journal of Laboratory and Clinical Medicine 120 (4) : 559-68 (1992).*

Database Biosis 'Online; Biosciences Information Service, Philadelphia, PA, US: 1990, Klepetko et al; Pulmonary Surfactant in Bronchoalveolar Lavage After Canine Lung Transplantation Effect of L Carnitine Application; Database Accession No. PREV199090067674; XP002215925.

Database Medline 'Online; Apr. 1994; Nakagawa et al; "The Effect of L-Carnitine on Myocardial Protection in Coid Cardioplegia Followed By Reperfusion"; Database Accession No. NLM8016834; XP002215926.

O. Ergun et al; "Carnitine as Preventive Agent in Experimental Renal Ischemia-Reperfusion Injury"; Urological Research, vol. 29, No. 3, Jun. 11, 2001, pp. 186-189, XP002215923.

U. Puetz et al; "Effects of L-Carnitine-Hydrochlorine in the Cold Ischemic Preservation of Fatty Liver Grafts"; Transplantion Proceedings, vol. 33, 2001, pp. 2523-2524, XP002215924.

Database Biosis Online; Biosciences Information Service, Philadelphia, PA, US; Mar. 2002, Mister Marilena et al; "Propionyl-L-Carnitine Prevents Renal Function Deterioration Due to Ischemia/Reperfusion"; Database Accession No. PREV200200206973, XP002215927.

Database Medline 'Online, 1992, Reckendorfer et al; "Hepatic Energy Metabolism During Hypothermic Storage and Reperfusion Using Different Protecting Solutions"; Database Accession No. NLM1292938, XP002215928.

Database CA 'Online; Chemical Abstracts Service, Columbus, Ohio, US; S. Skrede et al; "Coenzyme a in Dog Kidneys During Hypothermic Perfusion"; Retrieved From STN-International Database Accession No. 99:67125 CA, XP002215929, 1983.

* cited by examiner

*Primary Examiner*—Sandra E. Saucier
(74) *Attorney, Agent, or Firm*—Nixon & Vanderhye P.C.

(57) ABSTRACT

A storage solution to maintain and perfuse organs awaiting transplantation comprising (a) an isotonic balanced solution comprising a physiologically acceptable amount of potassium, mono acidic phosphate, biacidic phosphate, chloride, sodium and bicarbonate ions; (b) 50-250 mM glucose; (c) 0.2-20 mM of an alkanoyl L-carnitine or a physiologically acceptable salt thereof; (d) 1-100 mM of L-carnitine or a physiologically acceptable salt thereof; (e) water is described. The storage solution can also include other components such as anti-oxidants and/or chelating agents.

4 Claims, 1 Drawing Sheet

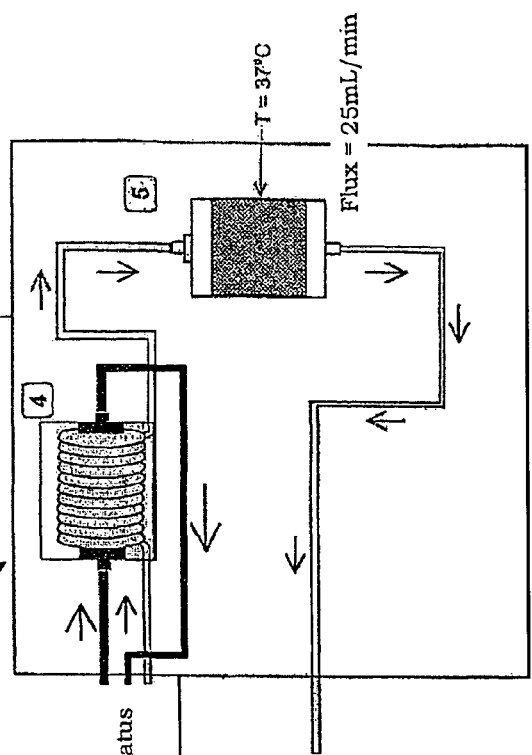
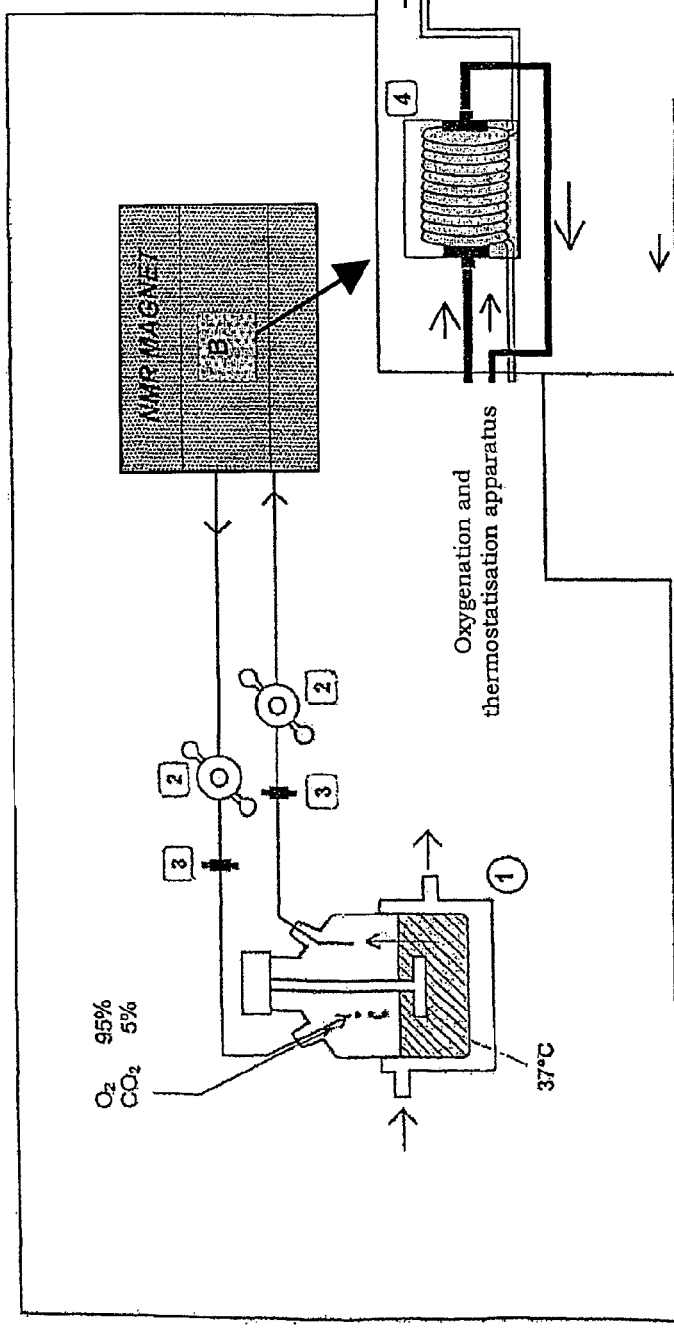
Figure 1a
Figure 1b
Oxygenation and thermostatisation apparatus
A:
1. Container
2. Peristaltic pump
3. Sampling port
B:
1. Heat/oxygen exchanger
2. Perfusion device

SOLUTION FOR THE STORAGE AND PERFUSION OF ORGANS AWAITING TRANSPLANTATION

This application is the US national phase of international application PCT/IT02/00391, filed in English on 13 Jun. 2002, which designated the US PCT/IT02/00391 claims priority to IT Application No. RM2001A000337 filed 14 Jun. 2001. The entire contents of these applications are incorporated herein by reference.

The present invention refers to a solution for the storage and perfusion of organs awaiting transplantation.

In the last 10 years, orthotopic organ transplant has become an irreplaceable therapeutic method for patients having particular, terminal stage organ diseases, such as for example hepatic, cardiac, pancreatic, pulmonary and renal diseases.

However, rejection of the transplanted organ continues to be a substantial problem.

For example, rejection contributes to a mortality rate of 15-25% during the first year after surgery in the case of liver transplantation (Strasberg S. M. et al, Hepatology 1994, 20: 829).

The phases in which the liver for transplantation undergo damage have been determined as:
1) Heat ischemia during the removal from the donor;
2) Cold ischemia during the hypothermic storage phase;
3) Reperfusion of the organ in the recipient; (Transplantation 53:957-978, 1992).

The basic strategy for the storage of organs for transplantation is that of slowing down the cellular catabolic processes through lowering the temperature of the organ from 37° C. to around 4-6° C. (hypothermia).

Hypothermia lowers the metabolic rate and the rate of hydrolysis catalysed by various intracellular enzymes, but does not completely inhibit cellular metabolism. This can bring about processes which lead to cellular alterations both in the endothelial sinusoidal compartment and in the hepatocytic compartment.

In fact, cooling of the isolated liver without perfusion results in a rapid reduction in ATP and ADP levels (J. Surg. Res. 23:339-347, 1977; Cryobiology 31:441-452, 1994) in as much as the residual energy demands exceed the cellular capacity to generate ATP through anaerobic glycolysis from glycogen reserves, with the consequent accumulation of lactic acid and intracellular acidosis.

The degradation of ATP to ADP and successively to AMP and adenine causes, dung hypothermia, an accumulation of hypoxanthine with the concomitant conversion of xanthine dehydrogenase to xanthine oxidase, and is associated with increases in intracellular calcium and protease activation (McCord J. M., N. Engl. J. Med. 1985, 312: 158).

In the reperfusion state, this results in degradation of hypoxanthine to xanthine and then to uric acid with the production of reactive oxygen intermediates (ROI) and oxidative type damage.

Furthermore, the diminished activity of enzymes, such as, for example, the Na/K ATPases results in changes in the conditions of electrolyte balance with consequent water influx and cellular swelling.

In recent years, a direct correlation between ATP content during hypothermic storage of the organ for transplantation, and the success of the transplant in humans has been demonstrated (Hepatology 1988, 8: 471).

To overcome such disadvantages, storage solutions whose composition has been studied to counteract the dangerous effects of anoxic hypothermia (during the storage phase) and of the normothermic reperfusion (during re-implantation phase) are used.

The formulation of such solutions is in continuous evolution to allow the improvement of the vital state of the organ and the increase of preservation times.

Solutions useful for the storage of organs awaiting transplantation are already known.

In Transplantation 2000 Apr. 15; 69(7):1261-5) it is reported that the solution from the University of Wisconsin, known as UW solution, is capable of retarding the catabolic processes and guaranteeing good preservation of the organs awaiting transplantation.

The composition of UW solution is based upon a pharmacological strategy, which intends to:
1) favor the re-synthesis of ATP through the addition of precursors such as adenine and phosphate;
2) prevent acidosis through the presence of phosphate buffer;
3) inhibit xanthine oxidase activity through allopurinol;
4) minimize the ionic redistribution using a composition similar to that found intracellularly (high K+); and above all
5) prevent cellular swelling through osmotic pressure, through the addition of lactobionate, raffinose and high molecular weight colloids, such as starch.

The basic strategy of this composition is however empirical, and it has been hypothesised that the effect could derive from a phenomenon known as "sum of protections" (Southard J. H. et al., Transplantation 1990, 49: 251).

In Transplant Proc. 1999; August; 31(5):2069-70 it is reported that the Celsior solution is useful for the storage of organs awaiting transplantation.

The saline solution EuroCollins is another known solution, useful for the storage of organs, having the composition reported in the following Table 1.

TABLE 1

| | Concentration |
|---|---|
| $K_2HPO_4 \cdot 3H_2O$ | 32 mM |
| $KH_2PO_4$ | 15 mM |
| KCl | 15 mM |
| $NaHCO_3$ | 10 mM |
| Glucose | 194 mM |

This solution has been considered for many years the standard solution in Europe for the storage of organs, in particular kidneys. Its formulation is based on obtaining an electrolytic composition is which simulates the intracellular environment. Further, in this solution, hypertonicity (420 mOsmol) is obtained by the addition of high glucose concentrations (around 190 mM).

The above-cited solutions are not without inconveniences, and have been subject to numerous modifications.

The principal disadvantages shown by UW solution lie in its high viscosity, with consequent possible damage, above all sustained by the endothelial cells, during perfusion of the organ, and in the high cost of each single component whilst remaining unsure as to their indispensability [Transplant Proc. 1999; August; 31(5):2069-70.

Celsior solution presents the disadvantage of not being a suitable solution for liver storage, if compared to solution UW [Transplant. 2000; Oct. 27;70(8):1140-2].

EuroCollins solution presents numerous disadvantages:
1—has a high glucose concentration which aggravates the problem of acidosis, due to the enormous production of lactate during hypothermic hypoxia;

2—does not prevent cellular swelling dug the storage of the organ;

3—is no better than solution UW (Transplantation 2000 Apr. 15; 69(7):1261-5).

The use of caritines in the medical field is already known.

In Ann. Thorac. Surg. 2001; 71:254-9 the use of L-carnitine for the treatment of cardioplegic ischemia, in isolated rabbit heart is described. This work reports that L-carnitine shows a protective effect on the recovery of cardiac functions in isolated rabbit heart, when this was perfused with whole blood in to which L-carnitine had been added.

The use of carnitine in the preparation of a solution for the storage of organs awaiting transplantation has never been previously described.

BRIEF DESCRIPTION OF THE DRAWINGS

FIG. 1a shows the oxygenation and thermostatisation apparatus; and

FIG. 1b is a detail of the measuring instrument.

DESCRIPTION OF THE INVENTION

It has now been found that the addition of carnitine and/or an alkanoyl L-carnitine to a storage solution for isolated organs exhibit a surprising capacity for storage and perfusion of organs, which is superior to that of the known solutions previously mentioned.

The solution according to the present invention differs from the known solutions by the presence of L-carnitine and/or an alkanoyl L-carnitine.

The solution according to the present invention is suitable for use in the storage and perfusion of organs awaiting transplantation.

Non-limiting examples of such organs are heart, liver, pancreas, lung and kidney.

Preferably, the solution according to the present invention comprises L-carnitine and an alkanoyl L-carnitine, in which the alkanoyl L-carnitine is selected from the group consisting of acetyl; propionyl; valeryl; isovaleryl; butiryl and isobutiryl L-carnitine.

In a general embodiment, the storage solution for maintaining and perfusing organs awaiting transplantation, according to the present invention comprises:
(a) a balanced isotonic solution comprising a physiologically acceptable quantity of potassium ions, mono-acidic phosphate, bi-acidic phosphate, chlorine, sodium, bicarbonate;
(b) 50-250 mM glucose;
(c) 0.2-20 mM alkanoyl L-carnitine or one of its physiologically acceptable salts; and/or
(d) 1-100 mM L-carnitine or one of its physiologically acceptable salts;
(e) water.

In a first preferred embodiment of the present invention the solution for the preservation and perfusion of organs awaiting transplantation (which will be hereinafter referred to as "Carnival Solution") has the composition reported in Table 2,

TABLE 2

| | Concentration |
|---|---|
| $K_2HPO_4 \cdot 3H_2O$ | 10-60 mM |
| $KH_2PO_4$ | 3-50 mM |
| KCl | 3-50 mM |
| $NaHCO_3$ | 2-50 mM |
| Glucose | 50-250 mM |

TABLE 2-continued

| | Concentration |
|---|---|
| Alkanoyl L-carnitine or one of its physiologically acceptable salts | 0.2-20 mM |
| L-carnitine or one of its physiologically acceptable salts | 1-100 mM |

Isovaleryl L-carnitine is the preferred alkanoyl L-carnitine.

By physiologically acceptable salt of L-carnitine or of an alkanoyl L-carnitine it is intended any salt thereof with an acid which does not give rise to undesired toxic effects. These acids are well known to pharmacologists and to experts in pharmaceutical technology.

Non-limiting examples of these salts are chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucosephosphate, tartrate, acid tartarate, magnesium tartrate, 2-amino ethanesulphonate, magnesium 2-amino ethanesolphonate, choline tartrate and trichloroacetate.

Fumarate is preferred.

An example of a preferred solution, according to the present invention is reported in table 3.

TABLE 3

| | Concentration |
|---|---|
| $K_2HPO_4 \cdot 3H_2O$ | 32 mM |
| $KH_2PO_4$ | 15 mM |
| KCl | 15 mM |
| $NaHCO_3$ | 10 mM |
| Glucose | 187.5 mM |
| Isovaleryl L-carnitine Fumarate | 2 mM |
| L-carnitine (inner salt) | 10 mM |

The solution according to the present invention can contain in addition:

1) One or more antioxidants, in useful amount to prevent the formation of free radicals derived from oxygen. Non-limiting exasemples of such antioxidants are: allopurinol, glutathione, beta-carotene, catalase, superoxide dismutase, dimethyl thiourea (DMTU), diphenyl phenylene diamine (DPPD), mannitol, cyanidanol; and vitamin E, and/or
2) dichioroacetic acid to reduce the lactate which is formed during the preservation.

The amount of antioxidants and/or dichloroacetic acid to be used is well known to the expert of the art, and widely reported in literature.

The solution according to the present invention is suitable to be used to prevent the mechanisms which cause damage to organs and therefore is a solution which (a) prevents or reduces intracellular acidosis; (b) prevents the damage caused by oxygen free radicals, in particular during reperfusion; (c) allows for the regeneration of high energy phosphates during reperfusion; (d) protects from expansion of the intracellular spaces; (e) sustains cellular metabolic requests.

The protective activity of the solution according to the invention has been evaluated in suitable experimental models, having as references known solutions, useful for the same purpose.

The following examples her illustrate the invention.

EXAMPLE 1

Many studies have demonstrated a correlation between the capacity of the transplant organ to regenerate high energy phosphorylated compounds, such as ATP, and the success of the transplantation. In fact, one of the most important aspects, for example in the storage of liver, is certainly the capacity for regeneration of high energy phosphorylated compounds, such as ATP, after the transplant, The high-energy phosphorylated compounds must be available for a large number of regulatory mechanisms which prevent cellular damage. For example, the levels of NTP (nucleoside triphosphates) in the liver must be in sufficient quantity to restore critical cellular processes, such as the maintenance of gradients which regulate the ion exchange across the plasma and mitochondrial membranes, protein synthesis, bile production and the urea cycle.

In the experimental trials carried out to demonstrate the efficacy of the solution according to the present invention, isolated rat livers were used, in which the alterations in ATP, ADP and total adeninic nucleotides (NTP) levels were analyzed, through spectroscopy $^{31}$P-NMR (J. Lab. Clin. Med. 1992, 120; 559; Transplantation 1994, 57: 1576), during cold ischemia, during the period of conservation, and during the reperfusion.

The realization of these experimental trials required the resolution of the following principal problems:
1) the construction of a perfusion chamber adapted to work inside an NMR magnet, and the creation of the pertinent perfusion circuit;
2) the construction of a radio frequency (RF) coil utilizable with the perfusion chamber;
3) the definition of times (duration of the perfusion, conservation and reperfusion phases; intervals to study through spectroscopy during each of these phases; minimum duration time of a single spectrum; optimization of the passage times from one phase to another).

Perfusion Circuit and Chamber

The diagram of the perfusion circuit is reported in FIG. 1.

The construction of this circuit was carried out taking into account that the appropriate temperature and oxygenation conditions must be maintained in the organ, which is located at a distance of several meters from the perfusion system, constituted of pumps and a thermostat. In fact, these instruments need to be positioned outside the magnetic field of the measuring instruments, corresponding to a minimum distance of 6 meters, in our case.

In FIG. 1a, 1 is the container, 2 is the peristaltic pump and 3 is the sampling port.

In FIG. 1b, 1 is the heat/oxygen exchanger and 2 is the perfusion device.

The perfusion medium KH (Krebs-Henseleit+glucose+ BSA) (400 ml) (Krebs H. A. 1930; Biochem. J. 98, 720; Henseleit K. 1932; Hoppe-Seylerr's Z. physiol. Chem. 210, 33.), placed in a thermostatic container, away from the magnets, was continuously mixed by magnetic stirring.

The thermostatisation was performed in so as to obtain a temperature of 37±0.5° C. in the perfusion chamber containing the organ inside the magnets.

Oxygenation of the medium was ensured through the use of a membrane oxygenator.

The oxygen saturation level was calculated on the basis of the permeability factor of the silicone used, the caliber and thickness of the tube, the flow rate and the length of the tube wrapped in a spiral inside the oxygenation and thermostatisation apparatus. The values calculated gave results between 30 and 35% $O_2$.

The perfusate was recycled with the aid of a peristaltic pump with a 25 ml/min flow rate.

The perfusion circuit used polyethylene tubes having a 1 mm inner diameter of and a length of 6 meters to and from the magnets.

To ensure the maintenance of a controlled temperature inside the perfusion chamber in the magnet, both the thermostatisation and perfusion circuits were made to pass jointly inside a thermo isolated neoprene tube.

The circuit was activated and stabilized at least one hour prior to the organ perfusion to ensure reaching the desired temperature and oxygenation.

The perfusion chamber, constructed in Perspex, was fixed to a PVC support to allow insertion inside the magnets. That had a cylindrical geometry, a diameter of 34 mm×65 mm in height.

The liver was maintained suspended at the desired height by fixing the cannula with appropriate distancing support disks. Drainage was performed by collecting the perfusion liquid in the funnel-shaped bottom, followed by aspiration to the collecting reservoir.

Normothermic damage by ischemia and reperfusion is a determining factor in the pathogenesis of hepatic damage, that arises during surgical procedures, such as hepatic resection and liver transplant.

In order to minimize as much as possible the heat ischemia time, variations to the standard surgical procedure of liver removal were introduced. In particular, non fasted animals were used; in animal models, in fact, studies in vivo and in vitro have demonstrated that fasting aggravates the normothermic ischemic damage caused by a reduction in glycogen content.

Male Wistar rats were used with initial body weights of 150 g. The animals were anaesthetized by an intraperitoneal injection (i.p.) of sodium thiopental, then subjected to a median incision with successive opening of the peritoneum.

The portal vein and the vena cava inferior were exposed, as much adherences and fat as possible were removed to make removal of the organ faster and minimize the time of ischemia.

Ligatures were prepared for the vena cava inferior and the portal vein.

The vena cava was closed followed by, in rapid succession, the portal vein.

A cannula was inserted into the portal vein (Abbocath-T 20G; Abbott) which was fixed with a previously prepared suture and connected to a syringe containing cold Ringers lactate solution (Dawson R. M. C. (ed.), Ellott D. C. Elliott W. H. and Jones K. M. (1969) Data for biochemical research, $2^{nd}$ ed. Clarendon Press, Oxford.) for a first blood washing perfusion. The vena cava was cut to allow the outflow of perfusion liquid.

Then the organ was removed as quickly as possible.

From closing the blood vessels to beginning the perfusion inside the magnets was a time interval no greater than 10 minutes, with 1-2 minutes of heat ischemia.

The cannula was left in situ and used for the reperfusion.

The experimental protocol followed is reported in the following diagram 1.

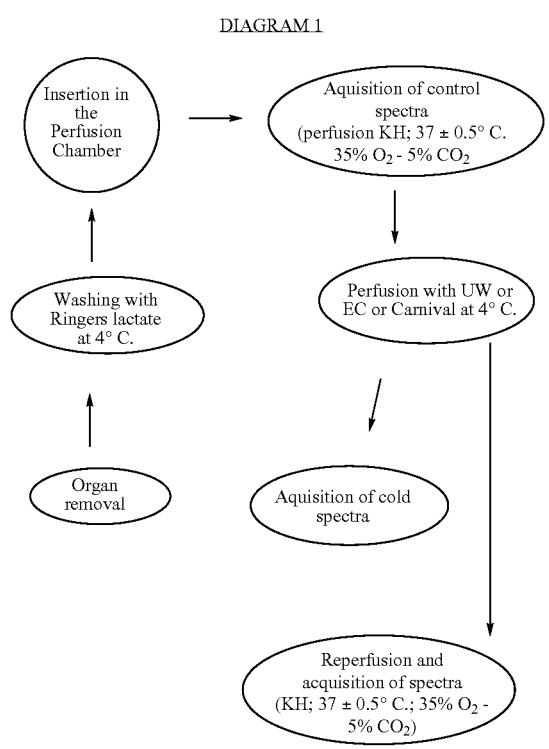

DIAGRAM 1

Livers were perfused in situ with Ringers lactate solution at 4° C. to eliminate the blood and to limit as much as possible the normothermic ischemia times of the organ.

The isolated organs were then placed in perfusion inside the magnets, in an appropriate bioreactor, fed with Krebs-Henseleit solution at 37° C., 35% $O_2$, for the acquisition of basal reference spectra $^{31}$P NMR (time 0).

The acquisition of these NMR spectra was carried out to eliminate the biological variability between organs; in this manner, in fact, the variations observed after preservation can be referred to values determined in the same organ immediately upon removal from the animal and stabilized in perfusion for 40'.

At the end of 40' stabilization, the organs were perfused with different storage solutions at 4° C.

The experimental tests were carried out using Carnival solution in accordance with the present invention, and two known storage solutions were used as reference:
1) UW solution with the addition of insulin (40 I.U./L) and dexamethasone (8 mg/L); and
2) EuroCollins solution.

Table 4 reports the compositions of Carnival, EuroCollins and UW solutions.

TABLE 4

|  | Carnival solution | EuroCollins solution | UW solution |
| --- | --- | --- | --- |
| $K_2HPO_4 \cdot 3H_2O$ | 32 mM | 32 mM | 2.5 mM |
| $KH_2PO_4$ | 15 mM | 15 mM | – |
| KCl | 15 mM | 15 mM | – |
| $NaHCO_3$ | 10 mM | 10 mM | – |
| Glucose | 187.5 mM | 194 mM | – |
| Isovaleryl L-carnitine | 2 mM | – | – |
| Fumarate |  |  |  |

TABLE 4-continued

|  | Carnival solution | EuroCollins solution | UW solution |
| --- | --- | --- | --- |
| L-carnitine (inner salt) | 10 mM | – | – |
| Glycine | – | – | 15 mM |
| Allopurinol | – | – | 1 mM |
| Adenosine | – | – | 2.5 mM |
| Lactobionate | – | – | 100 mM |
| $MgSO_4 \cdot 7H_2O$ | – | – | 5 mM |
| Raffinose | – | – | 30 mM |
| PEG\ | – | – | + |

"–" means "absent";
"+" means "present".

In some experiments spectra were acquired cold, immediately after perfusion of the organ with the solution in accordance with the present invention, to evaluate the kinetics of the disappearance of phosphorylated metabolites in the $1^{st}$ hour.

The results obtained are reported in tables 8-10.
For each spectrum it was noted:
1) the total levels of phosphorylated metabolites;
2) the levels of inorganic phosphate and phospho monoesters (Pi+PME);
3) the levels of nucleoside triphosphates (NTP);
4) the levels of NAD as the sum of the signals α–NTP+NAD.

The spectra were acquired at 10-minute intervals over one hour.

The livers were stored by immersion in several solutions at 4° C. for a total time of 26 hours.

The storage time was chosen in order to evaluate the restating capacity after a much longer time than that normally used in clinical practice or in experiments.

At the end of the storage time (26 ore), the livers were again placed inside the magnets in perfusion with solution KH, at 37° C., 35% $O_2$, to monitor the phosphorylated metabolites.

$^{31}$P-NMR spectra were acquired every 15' over a time limit of 140'.

The results obtained are reported in tables 5-7.

NMR Experimental Conditions

The specific characteristics of the $^{31}$P-NMR experiment strictly depended on the experimental configuration chosen for liver perfusion, with the main objective of obtaining spectra having optimal signal/noise ratios.

The salient difficulties to take into consideration were:
i) the necessity to use brief scanning times;
ii) optimization of the operating conditions of the Nuclear Magnetic Resonance system;
iii) heterogeneity in the geometry and composition of the samples.

The experimental conditions utilized were:
spectral bandwidth 8.33 KHz;
sampling 2048 points;
acquisitions 900;
dummy scan 2;
2-step phase cycle;
impulse at 90 ° (150 µs);
2 s repetition interval.

The spectra, in relation to the diverse experimental conditions were obtained from the accumulation of 450 scans in conditions of perfusion or reperfusion and of 300 scans in conditions of hypothermia, always with a repetition time of 2 seconds.

The $^{31}$P-NMR spectra obtained display signals relative to α, β and γ phosphate of the nucleotide triphosphates respectively at −9.7, −18.35 and −4.2 ppm and are prevalently represented by adenosine triphosphate (ATP) and in minor amounts by guanosine triphosphate (GTP), uridine triphosphate (UTP) e cytidine triphosphate (CTP).

The signal assigned to αNTP is contributed to by the resonance of the nicotinamide-adenine-dinucleotide phosphates (NAD) and nicotinamide-adenine-dinucleotide phosphate.

The signals relating to α and β phosphates of the nucleotide diphosphates, mainly represented by adenosine diphosphate (ADP), are respectively at −8.9 and −4.4 ppm. This last signal is partially masked by the signal from γNTP.

The signals at −11.5 ppm attributed to compounds having two di-esterified phosphate groups (DPDE) are mostly represented by uridine diphosphoglucose and uridine diphospho glucuronate.

Signals relating to phospholipid intermediates are present in the spectral zone between 5.8 and 4 ppm, where the nuclei of phosphate groups from monophosphate esters (PME) resonate.

300 mM methylene diphosphonate (MDP) contained in a capillary (0.5 ml) fixed to the inside of the perfusion chamber, was used as a reference.

The signal area was evaluated by applying one of the known programs for the reconstriction of resonance spectra (program SPEC ANA; SMIS).

Results Obtained

The initial perfusion with KH solution (37° C., 35% $O_2$) after removal and washing of the liver with Ringers lactate solution (4° C.) for 40', was deemed sufficient for the stabilization of phosphorylated metabolite levels.

The initial levels (pre-storage) of β-ATP resulted as being 8.3±3.1, these for α-ATP of 22.6±5.4 respectively (whilst the values reported in the table are expressed as a percentage of the reference).

The ratios β-ATP/Pi+PME, α-ATP/Pi+PME and β-ATP/α-ATP gave results respectively of 8.4±5, 23.4±10.2 and 35.7±11.

The values thus obtained were used as reference for time 0 for the subsequent evaluations.

In Table 5 the results relating to a representative spectrum obtained previously, during and after preservation with Carnival solution are reported.

TABLE 5

| TIMES | β | γ | α |
|---|---|---|---|
| Stabilisation of levels; (NMR analysis after explant, washing, perfusion with KH, at 37° C.) | | | |
| 40' | 8.9 | 10.3 | 27.5 |
| Perfusion with Carnival solution and storage at 4° C.; NMR analyses were performed at 4° C. at the times indicated below | | | |
| 10' | n.d. | n.d. | 58% |
| 20' | n.d. | n.d. | 74% |
| 30' | n.d. | n.d. | 69% |
| 40' | n.d. | n.d. | 65% |
| 50' | n.d. | n.d. | 67% |
| 60' | n.d. | n.d. | 71% |
| The organs were conserved immersed in Carnival solution, at 4° C., for further 25 hours The organs were then perfused at 37° C. with KH solution; NMR analyses were performed at 37° C. at the times indicated below | | | |
| 30' | 84% | 68% | 90% |
| 45' | 81% | 81% | 87% |
| 60' | 109% | 75% | 99% |
| 75' | 112% | 97% | 83% |
| 90' | 71% | 83% | 70% |
| 105' | 99% | 85% | 87% |

TABLE 5-continued

| TIMES | β | γ | α |
|---|---|---|---|
| 120' | 101% | 68% | 68% |
| 135' | 72% | 69% | 75% |

The values relating to after explant are expressed as ratios of the reference signal. All other values are expressed as percentages with respect to the latter.

In Table 6, data relating to a previously obtained representative spectrum, during and after storage with UW solution, are reported.

TABLE 6

| TIMES | β | γ | α |
|---|---|---|---|
| Stabilisation of levels; (NMR analyses after explant, washing, perfusion with KH, at 37° C.) | | | |
| 40' | | 4.8 | 21.8 |
| Perfusion with UW solution and storage at 4° C.; NMR analyses were preformed at 4° C. at the times indicated below | | | |
| 10' | 51% | 71% | 117% |
| 20' | 28% | 56% | 96% |
| 30' | n.d. | 64% | 95% |
| 40' | n.d. | 80% | 128% |
| 50' | n.d. | 44% | 75% |
| 60' | n.d. | n.d. | 81% |
| The organs were stored immersed in UW solution, at 4° C., for a further 25 hours The organs were then perfused at 37° C. with KH solution; NMR analyses were performed at 37° C. for the times indicated below | | | |
| 30' | 51% | 49% | 79% |
| 45' | 45% | 56% | 70% |
| 60' | 91% | 74% | 90% |
| 75' | 79% | 62% | 81% |
| 90' | 65% | 94% | 75% |
| 105' | 58% | 58% | 86% |
| 120' | 56% | 91% | 83% |
| 135' | 44% | 73% | 64% |

Values relating to after explant are expressed as a ratio of the reference signal. All other values are expressed as a percentage of the latter.

In table 7, data relating to a previously obtained representative spectrum, during and after storage with EuroCollins solution, are reported.

TABLE 7

| TIMES | β | γ | α |
|---|---|---|---|
| Stabilisation of levels; (NMR analyses after explant, washing, perfusion with KH, at 37° C.) | | | |
| 40' | 7.9 | 6.1 | 25.6 |
| Perfusion with EuroCollins solution and storage at 4° C.; NMR analyses were performed at 4° C. at the times indicated below | | | |
| 10' | n.d. | n.d. | 96% |
| 20' | n.d. | n.d. | 69% |
| 30' | n.d. | n.d. | 67% |
| 40' | n.d. | n.d. | 58% |
| 50' | n.d. | n.d. | 65% |
| 60' | n.d. | n.d. | 51% |
| The organs were stored immersed in EuroCollins solution, at 4° C., for a further 25 hours The organs were then perfused at 37° C. with KH solution; NMR analyses were performed at 37° C. at the times indicated below | | | |
| 30' | 0% | 0% | 0% |

The values relating to after explant are expressed as ratios of the reference signal. All other values are expressed as percentages of the latter.

In table 7, data from a single reperfusion (30') spectrum are reported since at this and subsequent times, no re-synthesis of phosphorylated compounds was observed.

The kinetics of the disappearance of phosphorylated metabolites observed in the first 60' of cold preservation has demonstrated that the signal of α-ATP+α-ADP+NAD is present until the end of the measurements for all the preservation solutions in a manner that varies from organ to organ.

The β-ATP signal was detectable up to a maximum time of 30' only with preservation with UW, whilst it was absent even at the first spectrum for EuroCollins and Carnival solutions.

The γ-ATP+β-ADP signals remained present up to 50' of acquisition, due however solely to the presence of ADP.

The residual quantity of phosphorylated metabolites at 60' did not correlate with the capacity for re-synthesis of ATP in the normothermic reperfusion after 26 hours of conservation in the different solutions.

In tables 8, 9 and 10 values with standard deviations for β-ATP and α-ATP acquired at 80' and 140' of normothermic perfusion after perfusion and at the beginning of the preservation at 4° C. (cold spectra, NMR analyses were performed about 2 hours after organ removal) in Carnival, UW and EuroCollins solutions respectively, are reported.

TABLE 8

| Solution | Time (min) | β-ATP (n = 8) | α-ATP (n = 8) |
|---|---|---|---|
| Carnival | 80' | 62.4 ± 24 | 62.4 ± 14 |
| Carnival | 140' | 55.2 ± 25.2 | 53.5 ± 15.6 |

(n is the number of animals used)

TABLE 9

| Solution | Time (min) | β-ATP (n = 8) | α-ATP (n = 8) |
|---|---|---|---|
| UW | 80' | 64.2 ± 13.1 | 55.2 ± 17 |
| UW' | 140' | 57.2 ± 13.5 | 63.4 ± 19 |

(n is the number of animals used)

TABLE 10

| Solution | Time (min) | β-ATP (n = 8) | α-ATP (n = 8) |
|---|---|---|---|
| Euro Collins | 80' | 15 ± 13.7 | 52 ± 14.4 |
| EuroCollins | 140' | N.D. | 25.4 ± 21 |

(n is the number of animals used)

The values are expressed as percentages with reference to the same signal acquired at 37° C. after explant.

As can be noted, the solution according to the present invention plays a protective role in cellular vitality during the phase of normothermic reperfusion of isolated liver permitting the re-synthesis of ATP which is comparable during the phase of normothermic reperfusion to that observed with UW. It is important to remark that the reappearance of signal, and therefore the capacity for re-synthesis, is faster for the organs stored in Carnival with respect to these stored in UW, where satisfactory re-synthesis is not observed up to 60'.

Vice versa, organs stored in EuroCollins solution do not demonstrate appreciable ATP levels in the times considered.

Furthermore, it should be underlined that the concentrations of the metabolites were maintained at comparable levels for UW and Carnival solutions up to 140'.

The solution according to the present invention, in the hypothermic storage phase, further prevents cellular swelling due to osmotic phenomena, as observed qualitatively, analogous to that obtained with UW solution with lactobionate, raffinose and glycine added.

The solution according to the present invention favors the maintenance of hepatic bioenergetic integrity even after 26 hours of hypothermic conservation providing, at lower cost, comparable results to these obtained with the more expensive UW.

The invention claimed is:

1. A solution comprising:

| | |
|---|---|
| a) $K_2HPO_4 \cdot 3H_2O$ | 32 mM |
| b) $KH_2PO_4$ | 15 mM |
| c) KCl | 15 mM |
| d) $NaHCO_3$ | 10 mM |
| e) glucose | 187.5 mM |
| f) isovaleryl L-carnitine fumarate | 2 mM |
| g) L-carnitine | 10 mM | to maintain a perfused organ awaiting transplantation wherein the organ is selected from the group consisting of heart, liver, pancreas, lung and kidney.

2. The solution according to claim 1 wherein the organ to be stored is liver.

3. The solution according to claim 1, further containing at least one anti-oxidant in an amount sufficient to inhibit the formation of oxygen-derived free radicals.

4. The solution according to claim 3, wherein the anti-oxidant is selected from the group consisting of allopurinol, glutathione, beta-carotene, catalase, superoxide dismutase, dimethyl thiourea (DMTU), diphenyl phenylene diamine (DPPD), mannitol, and cyanidanol.

* * * * *